US00PP08896P

United States Patent [19]

Wu

[11] Patent Number: Plant 8,896

[45] Date of Patent: Sep. 13, 1994

[54] BUFFALOGRASS PLANT CALLED 'HILITE' 15

[75] Inventor: Lin L. Wu, Davis, Calif.

[73] Assignee: The Regents of the University of California, Oakland, Calif.

[21] Appl. No.: 143,317

[22] Filed: Oct. 25, 1993

[51] Int. Cl.[5] ..... A01H 5/00

[52] U.S. Cl. ..... Plt./90

[58] Field of Search ..... Plt. 90

[56] References Cited

PUBLICATIONS

Stebbins, G. L., (1975) "The Role of Polyploid Complexes in teh Evolution of North American Grasslands", *Taxon*, 24(I):91–106.

Reeder, J. R., (1971) "Notes on Mexican Grasses IX Miscellaneous Chromosome Numbers–3", *Brittonia* 23:105–117.

Wu, L., et al., (1994) "Identifying Buffalograss [*Buchloe dactyloides* (Nutt.) Engelm.] Cultivar Breeding Lines Using Random Amplified Polymorphic DNA (RAPD) Markers", *J. Am. Soc. Hort. Sci.* 119(1): 126–130.

*Primary Examiner*—James R. Feyrer

*Attorney, Agent, or Firm*—Townsend and Townsend Khourie and Crew

[57] ABSTRACT

A vegetatively reproduced perennial buffalograss cultivar was developed through mass selection from diploid (2n=20) buffalograss germplasms which is named 'Hilite' 15. It is distinguished by its fine texture, high turf density, rapid stolon spreading rate, competitive growth, short height growth, improved winter green color and short winter dormancy, summer turf quality, drought tolerance, low maintenance requirements, and improved turf performance.

3 Drawing Sheets

1

BACKGROUND OF THE INVENTION

Buffalograss, *Buchloe dactyloides* (Nutt) Engelm., is a warm-season stoloniferous, sod-forming, perennial grass. It is a drought tolerant and important range grass found mainly in the central prairies of the United States with its full range of distribution extending from Canada to Mexico (U.S. Agriculture Handbook, 1959). The buffalograss is the only species of its genus. It contains diploid, tetraploid, and hexaploid races (Stebbins, 1975), of which only the latter occur in the Great Plains area.

The diploid race mainly occurs in Central Mexico and sourthern Texas (Reeder, 1971) and it has rarely been researched for economical values.

'Hilite' 15 buffalograss [(*Buchloe dactyloides* (Nutt) Engelm.] is a vegetatively propagated, drought and heat resistant female buffalograss clone selected by mass selection. For breeding purposes, seeds of diploid buffalograss germplasms were collected from three locations in Central Mexico, including San Jose, San Clayetano, and Venegas. The population sizes for the three populations used for the first selection cycle were 215 for the San Jose population, 350 for the San Clayetano population, and 300 for the Venegas population, because a limited number of seeds was available.

Plants were established from seeds and space planted in the experimental field at UC, Davis. The plants were mowed weekly at a 2 inch height during the growing season (from May to the end of October). Individual clones were selected from rapid vegetative growth, high turf density, and extended winter turf green color. About 80% of the plants were eliminated in the selection for the above characteristics. The remaining plants were subjected to drought stress during the following summer months by terminating the irrigation for a period of 8 weeks (from June 15th, to August 15).

Two male and two female plants from each of the three populations were selected for their superior performance under the drought stress. For the second

2 selection cycle, a mass cross was constructed by growing the selected six male and six female clones close together in the field and seeds were harvested from the female plants. Six hundred plants were propagated from the seed progeny, were space planted in the field and were subjected to turfgrass management. Through the growing season, the plants were mowed weekly at 2 inch height, irrigated every 10 days with one pound N applied in June and 1 pound N applied in August. This female clone, named 'Hilite' 15, was selected for its superior performance in rate of vegetative growth, high turf density, retention of green color above freezing temperature, and superior drought tolerance. Asexual propagation was accomplished by vegetative reproduction from stolons, sprigs, plugs, and spreads of stolonization. Initially the plant was asexually reproduced in the greenhouse of The Department of Environmental Horticulture, University of California, Davis campus, Davis, Calif. Thereafter, such reproduction was tested at the University of California Davis campus and at the Santa Clara field station of Northern California.

Figure 1:
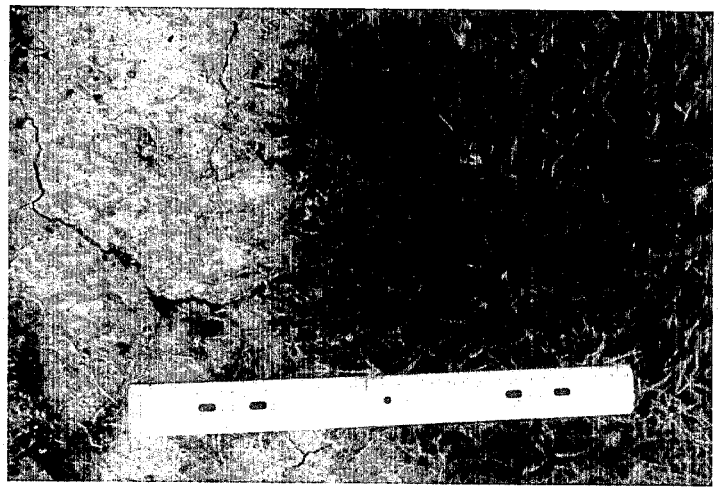
FIG. 1 depicts field grown buffalograss of the new variety and shows its high turf density, extensive vegetative growth, and short stolon internode characteristics.
Figure 2:
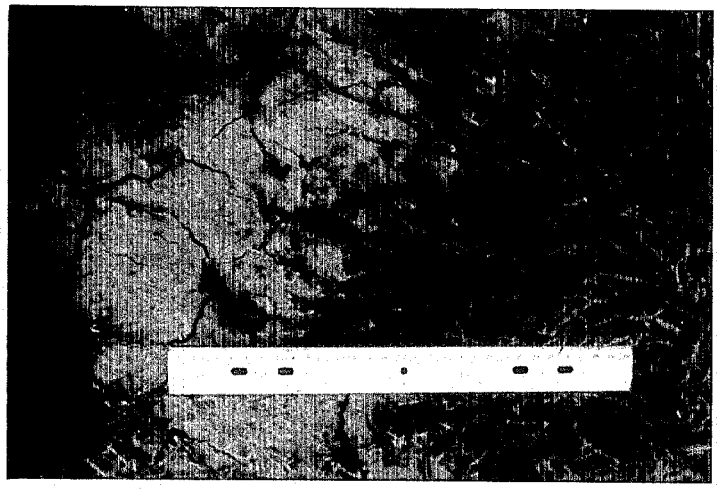
FIG. 2 depicts the turf growth habit, coarse texture, and long stolon internode of the field grown forage type 'Texoka' buffalograss.
Figure 3:
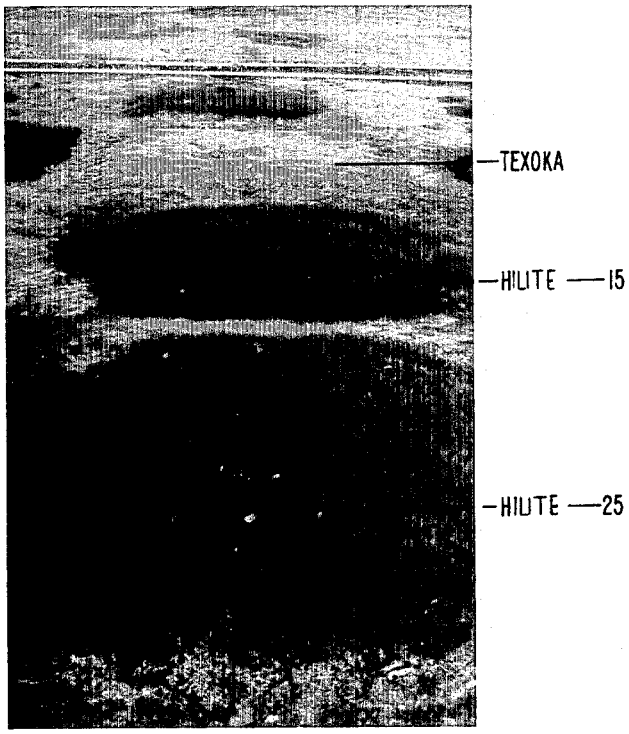

FIG. 3 depicts this variety and the 'Hilite' 25 variety compared with 'Texoka'. This variety obtained turf green color in mid-December at a temperature of 0° C. The low temperature sensitive 'Texoka' at the same time and temperature became dormant and brown.

Figure 4:
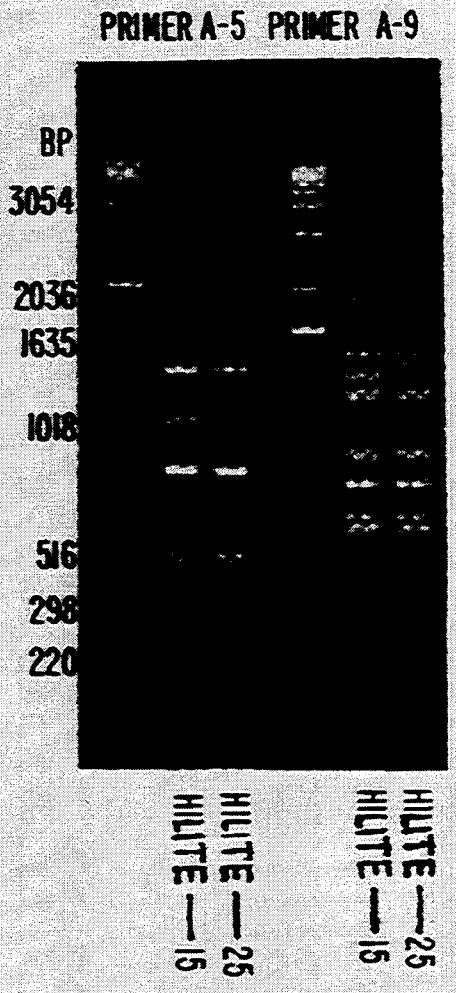

FIG. 4 depicts distinct DNA fingerprints detected from the vegetatively propagated 'Hilite' 15 and 'Hilite' 25 buffalograss varieties using RAPD markers produced by primers A-5 and A-9.

Existing buffalograss varieties such as 'Texoka', 'Sharps Improved', and 'Comanche' are reproduced sexually. These buffalograsses were developed for forage rather than turf purposes and are produced and distributed as seed commodity. These buffalograsses lack uniformity and density because the genetic variation exists in the seed progenies. In comparison to the existing vegetatively propagated tetraploid buffalograss 'Prairie' (2n=40), the 'Hilite' 15 is a diploid (2n=20) and has a short winter dormancy in the transition zone such as in California, a faster vegetative spreading rate, finer leaf blade, and thinner stolon textures.

SUMMARY OF THE INVENTION

The 'Hilite' 15 buffalograss clone is a diploid with a chromosome number of 20. It is fine-textured, with stolon diameters of approximately 0.8 mm. Leaf width is approximately 1.5 mm and leaf length is about 90 mm. In comparison to the 'Texoka' and 'Prairie', the 'Hilite' 15 buffalograss exhibits shorter internode length, smaller internode diameter, faster stolon growth rate does not possess pubescence on the leaves, and has considerably less winter dormancy. 'Texoka' is a hexaploid seeded cultivar and it has 60 chromosomes. 'Prairie' is a vegetatively propagated cultivar and has 40 chromosomes. Based upon the Inter-Society Color Council-National Bureau of Standards Color Chart, September 1988, (ISCC-NBS Color) 'Hilite' 15 has a deep green color (118 deep YG), rapid spreading stoloniferous grwoth habit and short vertical growth. It is heat and drought resistant with excellent drought avoidance characteristics (fast recovery from dormancy due to drought).

DETAILED DESCRIPTION OF THE PLANT

'Hilite' 15 is particularly adaptable to areas of the California central valley and sourthern California, the transition zone and from Central Mexico to the central Great Plains of the United States. Its growth is best in direct high sunlight with temperatures above 20° C. Its performance under shaded conditions is comparable to bermudagrasses.

'Hilite' 15 may be established by planting sod, springs, or plugs. Planting 2 inch prerooted plugs on 12 inch centers establishes 'Hilite' 15 turf within 10 weeks (from June to August). It is a female plant which is a vegetatively propagated clone and spreads by stolonization. 'Hilite' 15 does not produce male inflorescences as appear in seeded buffalograss. Nor does it produce viable seed in the absence of pollination. It forms a dense, uniform, fine-textured, stoloniferous, deep green turf. In the absence of mowing, 'Hilite' 15 reaches a mature height to 10 to 15 centimeters. It requires minimal water, nutrition, and other maintenance. 'Hilite' 15 s dense and aggressive growth characteristics render it far more competitive against weeds. In 'Hilite' 15, aesthetic attributes of density, uniformity, and appealing turf color combine with durability, competitiveness and low maintenance requirements. Together, these agronomic attributes render 'Hilite' 15 particularly suitable for home lawns, recreational turf such as golf courses, industrial parks and ground cover for roadsides. 'Hilite' 15 is more distinctly characterized in the following chart and tables, as observed in greenhouse and open field testing studies at the experimental field at the University of California and the Field Stations in northern and southern California.

The color of 'Hilite' 15 is deep green (118 deep YG) when in season, to yellow (73.p.OY), when in dormancy.

The characteristic differences between 'Hilite' 15 and another newly developed vegetatively propagated diploid buffalograss called 'Hilite' 25 are: (2) 'Hilite' 25 produces a higher turf density than 'Hilite' 15' but, it is less salt tolerant than 'Hilite' 15. (1) 'Hilite' 15 and 'Hilite' 25 are similar in turf density and morphological characteristcis, but 'Highlight 25' displays a better spring turf quality, and 'Highlight 15' has a better summer turf quality. (3) Random primer amplified DNA fragment finger print analysis was performed using random primers A-5 and A-9 (Promega). The two 'Hilite' buffalograss cultivars are found to differ in DNA fingerprint genetic markers.

The Variety

Origin: A single superior diploid female buffalograss plant selected from mass crosses of three diploid buffalograss germplasms collected from central Mexico.

Classification:

*Botanical.*—*Buchloe dactyloides* (Nutt.) Engelm.

Chromosome number: 2n=20.

Form: Monocot Gramineae.

Growth habit: A stoloniferous vegetatively reproducing female plant with short vertical growth and rapid horizontal growth rate. Its fibrous root system knits in most media within three weeks from plugs or stolon cuttings. In season, it produces dense, uniform, fine textured turf and holds its green color near freezing temperature during the winter months.

Establishment rate:

*Sod.*—1–2 weeks.

*Plugs.*—6–8 weeks (in July and August).

*Springs.*—6–8 weeks.

Regions of adaptation: From central Mexico to the central Great Plains of the United States and particularly adaptable to areas of the California Central Valley and southern California.

*Blade.*—Shape — Long, slender, pointed leaf tip.

*Length.*—About 5 to 10 cm long with an average of 8 cm.

*Width.*—About 0.15 cm.

*Hairiness.*—Absent, glabrous.

Mature plant height: 10 to 15 cm.

Internode:

*Length.*—6 to 7 cm (average of 6.5 cm) between the 2nd and third nodes from the tip of stolon, about 60% shorter than 'Prairie' buffalograss.

*Diameter.*—0.1 to 0.15 cm in the third internode from the tip of a stolon.

Node pigmentation: Purple (262.gy.pR).

Stolon color: Green (120.m.YG).

Leaf color:

*Active.*—Deep green (118 deep YG).

*Dormant.*—Yellow (73.p.OY) to brown.

Soils: Heavy clay, silty clay, loam, calcareous, neutral to alkaline.

Inflorescence:

*Male.*—Absent.

*Female.*—0.45 to 0.55 cm long.

TABLE 1

Relative Performance of 'Highlight' 15 in Comparison to Other Varieties for the Following Characteristics.

| Character (1 to 9 scale, 9 = best, 0 = not tested) | 'Hilite' 15' | 'Hilite' 25 | 'Prairie' | 'Texoka' |
|---|---|---|---|---|
| Rate of Spread | 9a | 9a* | 7b | 4c |
| Turf density | 8a | 9a | 7b | 3c |
| Drought tolerance | 9a | 9a | 9a | 7b |
| Injury regrowth potential | 8a | 8a | 7b | 4c |
| Shade tolerance | 4a | 4a | 4a | 3b |
| Color | 7a | 7a | 4b | 5c |
| Cold tolerance | 9a | 9a | 9a | 7b |
| Heat tolerance | 9a | 9a | 9a | 7b |
| Salinity tolerance | 6a | 4b | 4b | 3c |

*Means separated by Duncan's new multiple range test, P = 1%.

TABLE 2

Mean Turfgrass Quality Ratings of 'Hilite' 15 in Comparison to Other Varieties Over a Period of One year Growing Season at Santa Clara, California.

| Mean Value (1 to 9 Scale, 9 = best) | MAY | JUN | JUL | AUG |
|---|---|---|---|---|
| 'Hilite 15' | 7.5a | 7.0a | 7.0a | 7.2a |
| 'Hilite 25' | 7.5a* | 7.3a | 7.0a | 7.3a |
| 'Prairie' | 6.0b | 6.5b | 6.5b | 6.5b |
| 'Texoka' | 4.5c | 4.7c | 5.7c | 5.7c |

| Mean Value (1 to 9 Scale, 9 = best) | SEP | OCT | NOV | MEAN |
|---|---|---|---|---|
| 'Hilite 15' | 7.5a | 7.1a | 7.0a | 7.1a |
| 'Hilite 25' | 7.5a | 7.1a | 7.0a | 7.2a |
| 'Prairie' | 6.3b | 5.3b | 4.0b | 5.8b |
| 'Texoka' | 5.0c | 3.3c | 1.0c | 4.2c |

Turfgrass quality is based on uniformity, density of stand, texture of turf canopy, smoothness of surface, and growth habit. (Beard, J. B., Turfgrass Science, 1973). Field trials were conducted at Davis and Santa Clara in northern California and at Riverside in southern California.

*Mean separated by Duncan's new multiple range test, P = 1%.

TABLE 3

Rate of turf establishment from two inch plugs (% coverage) of 'Hilite 15' and 'Hilite 25' buffalograsses in comparison to 'Prairie' and 'Texoka' buffalograsses

| | Date of Observation | | | | |
|---|---|---|---|---|---|
| Cultivar | 6/1/91* | 6/16/91 | 6/30/91 | 7/15/91 | 7/30/91 |
| 'Hilite 15' | 9a | 32a | 70a | 96a | 100a |
| 'Hilite 25' | 10a** | 30a | 70a | 95a | 100a |
| 'Prairie' | 5b | 16b | 35b | 46b | 70b |
| 'Texoka' | 4b | 9c | 18c | 25c | 45c |

*First observation conducted two weeks after planting of plugs in the field at Davis California.

**Mean separated by Duncan's new multiple range test, P = 1%.

TABLE 4

| | Morphological Description | | | |
|---|---|---|---|---|
| | 'Hilite' 15 | 'Hilite' 25 | 'Prairie' | 'Texoka' |
| A. Vegetative Traits (P = present, A = absent) | | | | |
| 1. STOLONS | P | P | P | P |
| a. Color or pigmentation | green (120.m.YG) | green (120.m.YG) | purple (262.gy.pR) | purple (262.gy.pR) |

TABLE 4-continued

| | Morphological Description | | | |
|---|---|---|---|---|
| | 'Hilite' 15 | 'Hilite' 25 | 'Prairie' | 'Texoka' |
| b. Internode length (mm) (third internode from the tip of the stolon) | 65 | 45 | 155 | 100 |
| c. Internode diameter (mm) | 0.55 | 0.55 | 0.9 | 0.9 |
| 2. NODES | | | | |
| a. Color or pigmentation | purple light (262 gY.pR) | purple (259.d.p R) | purple (259.d.p.R) | purple (259.d.p.R) |
| 3. RHIZOMES | A | A | A | A |
| 4. LEAF BLADE | | | | |
| a. Color: | | | | |
| (1) Dormant | yellow (73.p.OY) | Yellow (73 p.OY) | yellow (73.p.OY) | yellow (73.p.OY) |
| (2) Active | deep green (118.deep Y G) | deep green (118.deep Y G) | blue green (164.m.bG) | blue green (164.m.bG) |
| b. Dimensions | | | | |
| (1) Width (mm) | 1.2 | 1.2 | 2.0 | 2.0 |
| (2) Length (cm) | 8 | 8 | 10.5 | 13.0 |
| c. Hairness: | | | | |
| (1) Abaxial | A | A | P(slight) | P |
| (2) Adaxial | A | A | P | P |
| 5. SHEATH (Adaxial margin): | | | | |
| a. Hairs | A | A | P | P |
| b. Length (mm) | 15 | 15 | 15 | 18 |
| 6. Collar | | | | |
| (1) Hairness: | A | A | P | P |
| B. Floral Traits (P = present, A = absent) | | | | |
| 1. MALE INFLORESCENCE | A | A | A | A |
| 2. FEMALE INFLORESCENCE | A | P | P | P |
| a. Stigma color: | purple | purple | purple | purple |
| b. Spikelet: | | | | |
| (1) Number of burrs: | 2 | 2 | 2 | 2 |
| (2) Burr length (mm) | 5 | 5 | 8 | 7 |
| (3) Bur width (mm) | 2.5 | 2.5 | 3.5 | 4.0 |
| (4) # Flwrs per Burr | 2.5 | 2.5 | 2.5 | 2.5 |

TABLE 5

Comparison of ploidy level and chromosome number for 'Hilite,' 'Prairie', and 'Texoka' buffalograsses

| Cultivar | Ploidy level | Chromosome number |
|---|---|---|
| 'Hilite' 15' | diploid | 20 |
| 'Hilite' 25' | diploid | 20 |
| 'Prairie' | tetraploid | 40 |
| 'Texoda' | hexaploid | 60 |

I claim:

1. I claim the new and distinct variety of buffalograss plant illustrated and described and having the characteristics above enumerated.

* * * * *